US010321936B2

(12) United States Patent
Backes (10) Patent No.: US 10,321,936 B2
(45) Date of Patent: Jun. 18, 2019

(54) POLYAXIAL PEDICLE SCREW WITH A HEAD IN THE SHAPE OF A BALL SEGMENT

(71) Applicant: NGMEDICAL GMBH, Nonnweiler-Primstal (DE)

(72) Inventor: Hermann Backes, Namborn (DE)

(73) Assignee: NGMEDICAL GMBH, Nonnweiler-Primstal (DE)

( * ) Notice: Subject to any disclaimer, the term of this patent is extended or adjusted under 35 U.S.C. 154(b) by 0 days.

(21) Appl. No.: 15/556,198

(22) PCT Filed: Mar. 16, 2016

(86) PCT No.: PCT/EP2016/055664
§ 371 (c)(1),
(2) Date: Sep. 6, 2017

(87) PCT Pub. No.: WO2016/146672
PCT Pub. Date: Sep. 22, 2016

(65) Prior Publication Data
US 2018/0049773 A1    Feb. 22, 2018

(30) Foreign Application Priority Data

Mar. 19, 2015  (DE) .................. 10 2015 003 574
Aug. 17, 2015  (DE) .................. 10 2015 010 741

(51) Int. Cl.
*A61B 17/70*    (2006.01)
*A61B 17/86*    (2006.01)

(52) U.S. Cl.
CPC ........ *A61B 17/7005* (2013.01); *A61B 17/704* (2013.01); *A61B 17/7035* (2013.01); *A61B 17/7037* (2013.01); *A61B 17/86* (2013.01)

(58) Field of Classification Search
CPC ............ A61B 17/7005; A61B 17/7035; A61B 17/7037; A61B 17/704
See application file for complete search history.

(56) References Cited

U.S. PATENT DOCUMENTS 7,722,649 B2    5/2010  Biedermann et al. ........ 606/257
8,449,577 B2 *  5/2013  Kloss ................. A61B 17/7037
                                                 606/264

(Continued)

FOREIGN PATENT DOCUMENTS

DE          9402695        4/1994   ............ A61B 17/70
DE         10236691       12/2005   ............ A61B 17/58

(Continued)

OTHER PUBLICATIONS

The Notification Concerning Transmittal of International Preliminary Report on Patentability (Chapter I of the Patent Cooperation Treaty), in English, dated Sep. 28, 2017, which was issued by the International Bureau of WIPO in Applicant's corresponding international PCT application having Serial No. PCT/EP2016/055664, filed on Mar. 16, 2016.

(Continued)

*Primary Examiner* — Julianna N Harvey
(74) *Attorney, Agent, or Firm* — Bodner & O'Rourke, LLP; Gerald T. Bodner; Christian P. Bodner (57) ABSTRACT

Polyaxial pedicle screw with a head in the shape of a ball segment and with a threaded screw shank, wherein a hollow ball segment with a recess for receiving a rod-shaped connector is mounted in the head, in order to permit pivoting movements and rotation movements of the connector, wherein moreover, in the direction of the longitudinal axis of the threaded screw shank, the head in the shape of a ball segment has a cutout with an inner thread in which the rod-shaped connector can be moved in and out and, by means of the inner thread in the cutout, a grub screw can be (Continued)

introduced for blocking the hollow ball segment. According to the invention, a plastic buffer body is fitted in the hollow ball segment and is connected to a ram, wherein the ram has a head which engages in an associated annular groove in the plastic buffer body. Moreover, the plastic buffer body has a circumferential guide ring and a spherical guide stop at one end, wherein an opening for the ram is formed lying opposite the guide stop, and the edge of the opening bears on a shell, which in turn bears on the inner side of the hollow ball segment, in such a way that the plastic buffer body with its guide stop is fixed with pretensioning in the head shaped as a ball segment.

13 Claims, 6 Drawing Sheets

(56) References Cited

U.S. PATENT DOCUMENTS

| | | | | |
|---|---|---|---|---|
| 2005/0085813 | A1* | 4/2005 | Spitler | A61B 17/1757 606/86 A |
| 2005/0192572 | A1* | 9/2005 | Abdelgany | A61B 17/7037 606/266 |
| 2006/0036244 | A1* | 2/2006 | Spitler | A61B 5/103 74/1 R |
| 2006/0149237 | A1* | 7/2006 | Markworth | A61B 17/7005 606/279 |
| 2006/0241600 | A1* | 10/2006 | Ensign | A61B 17/7005 81/52 |
| 2006/0254784 | A1 | 11/2006 | Hartmann et al. | 172/789 |
| 2007/0198014 | A1* | 8/2007 | Graf | A61B 17/7005 623/17.16 |
| 2007/0213719 | A1* | 9/2007 | Hudgins | A61B 17/7005 606/278 |
| 2008/0167688 | A1 | 7/2008 | Fauth et al. | 606/265 |
| 2008/0183214 | A1* | 7/2008 | Copp | A61B 17/7005 606/265 |
| 2009/0312804 | A1* | 12/2009 | Gamache | A61B 17/704 606/308 |
| 2010/0228292 | A1* | 9/2010 | Arnold | A61B 17/7005 606/264 |
| 2012/0083845 | A1 | 4/2012 | Winslow et al. | 606/264 |
| 2012/0239090 | A1* | 9/2012 | Abdou | A61B 17/7005 606/264 |
| 2016/0338739 | A1* | 11/2016 | Juchno | A61B 17/7001 |

FOREIGN PATENT DOCUMENTS

| | | | |
|---|---|---|---|
| DE | 102005005647 | 8/2006 | A47L 5/32 |
| DE | 102012202750 | 8/2013 | A61B 17/70 |
| EP | 1388323 | 2/2004 | A61B 17/58 |
| WO | WO2005023125 | 3/2005 | A61B 17/70 |

OTHER PUBLICATIONS

The English translation of the International Preliminary Report on Patentability (Chapter I of the Patent Cooperation Treaty), dated Sep. 19, 2017, which was issued by the International Bureau of WIPO in Applicant's corresponding international PCT application having Serial No. PCT/EP2016/055664, filed on Mar. 16, 2016.

The Written Opinion of the International Searching Authority, in English, dated Jun. 20, 2016, which was issued by the International Bureau of WIPO in Applicant's corresponding international PCT application having Serial No. PCT/EP2016/055664, filed on Mar. 16, 2016.

The International Search Report, in English, dated Jun. 20, 2016, which was issued by the International Bureau of WIPO in Applicant's corresponding international PCT application having Serial No. PCT/EP2016/055664, filed on Mar. 16, 2016.

* cited by examiner

POLYAXIAL PEDICLE SCREW WITH A HEAD IN THE SHAPE OF A BALL SEGMENT

The invention relates to a polyaxial pedicle screw with a head in the shape of a ball segment and with a threaded screw shank, wherein a hollow ball segment with a recess for receiving a rod-shaped connector is mounted in the head, in order to permit pivoting movements and rotation movements of the connector, wherein moreover, in the direction of the longitudinal axis of the threaded screw shank, the head in the shape of a ball segment has a cutout with an inner thread in which the rod-shaped connector can be moved in and out and, by means of the inner thread in the cutout, a grub screw can be introduced for blocking the hollow ball segment according to the preamble of claim 1.

From DE 10 2012 202 750 A1, a dynamic stabilization device for bones, in particular for the spinal column is already known. The stabilizing system comprises two receiving elements in addition to a resilient element. The receiving elements are supported to be mutually displaceable and permit movements in the tension and compression directions of the implant. The receiving elements are configured by means of support surfaces and hook-like mating surfaces such that the resilient element between the receiving elements is only subjected to compressive load even when the connecting element as a whole is under tensile load. The spring element may consist of a spiral spring, a cup spring or an elastic polymer having a solid or hollow cross-section. Ends of the receiving elements are fixed in U-shaped recesses of a screw head of a pedicle screw, the pedicle screws comprising a threaded screw shank. The rod-shaped ends of the receiving elements are fixed and immovable with respect to the position within the screw head.

In the dynamic stabilization device for bones according to DE 102 36 691 B4, at least one first and at least one second bone anchoring element is provided, each having a first section for anchoring in a bone and a second section for connecting to a rod. The bone anchoring elements are connected via a rod, wherein this connection is displaceable in the direction of the rod axis, and at least one of the bone anchoring elements is provided as a polyaxial bone screw. An element which can be elastically pre-tensioned in the direction of the rod axis may be provided between the bonde anchoring elements. The polyaxial bone screws employed are such polyaxial bone screws which have the shape of a ball segment at the screw head side, wherein the corresponding ball segment is surrounded by a sleeve which in turn serves the purpose of fastening the rod. The rod fixing is performed by screwing in an inner screw. In one embodiment, the inner screw comprises a sliding bottom so as to enable low-friction movement of the rod.

The generic DE 10 2005 005 647 A1 is based on a device for stabilizing the spinal column, comprising at least two pedicle screws and at least one connecting element in between. The pedicle screws therein associate the benefits of a monoaxial screw with those of a polyaxial screw in that the screw head is supported to be immobile on the screw shank so as to guarantee optimum repositioning of the vertebrae, and a movable ball segment being located in the screw head which facilitates the inserting of the connecting element passing through the screw heads and can rigidly fix it after the inserting has been completed.

In this regard, the pedicle screw described in more detail in DE 10 2005 005 647 A1 comprises a screw shank and a screw head with two opposed oblong hole-shaped recesses. A ball element with a recess for accommodating a rod-shaped connecting element is movably mounted in the screw head. This ensures that the ball element is able to adapt to the position of the inserted connecting element in the anteflexion and retroflexion directions and to enclose it after the fixing has been completed. The screw head itself is hollow so as to receive the ball element which enables rotational movements of an inserted connecting element in the screw head about a lateral axis. In order to allow the penetrating connecting element to perform these movements, the screw head exhibits two oblong hole-shaped opposed openings within which the tilting movements or inclining movements of the connecting element can be realized. This results in a preferred cylindrical or oval configuration of the screw head. Medical-grade stainless steel, titanium or titanium alloys, tantalum, but plastic as well are used as a material for the prior pedicle screws.

The solutions mentioned above thus show movable ball segments for angular variability, elastic properties, however, being not given. It is true that solutions with spring elements which are formed between the connecting rods of an implant guarantee a corresponding elasticity for the purpose of dynamically stabilizing corresponding vertebral bodies, however, such spring elements that are present between the rods occupy a volume that cannot be neglected, which should be avoided in principle.

From the afore-mentioned, it is therefore the task of the invention to propose a further developed polyaxial pedicle screw with a head in the shape of a ball segment and with a threaded screw shank, wherein, in the implanted state, a physiological movement should be possible by an optional change of length and simultaneous tilting of rod-shaped connectors in relation to the fixed pedicle screw. In this manner, the arrangement of pedicle screws and connectors may absorb and follow the movements of the spinal column such as flexion, extension, lateral tilt and rotation.

The task of the invention is solved by the feature combination according to the teaching of claim 1, the dependent claims comprising at least purposeful configurations and improvements.

The inventive approach in forming the special polyaxial pedicle screw with the head in the shape of a ball segment is to concentrate all necessary functions including the accommodation and guidance of rod-shaped connectors in addition to the desired damping properties with targeted movability in the screw head itself so that elastic means otherwise inserted between the connectors may be omitted.

The invention solves the problem of known systems which is that such constructions occupy so much space that in case of tightly close pedicles, such as is the case in the lowermost segment L5/S1, for example, an implantation is almost impossible.

Consequently, a polyaxial pedicle screw with the head in the shape of a ball segment and with a threaded screw shank is taken as a basis, wherein a hollow ball segment with recesses for accommodating the rod-shaped connector is mounted in the head. The hollow ball segment permits pivoting and rotational movements of the connector.

In the direction of the longitudinal axis of the threaded screw shank, the head in the shape of a ball segment has a cutout with an inner thread, into and out of which cutout the rod-shaped connector can be pivoted. A grub screw which can be introduced into the inner thread of the cutout, enables blocking of the hollow ball segment.

According to the invention, an elastic plastic buffer body is fitted in the hollow ball segment and is connected to a ram, wherein the ram has a head which engages in an associated annular groove in the plastic buffer body.

In a preferred embodiment, the head of the ram is ovbermolded by the plastic buffer body and in this respect connected to the same in a form-fit manner.

Moreover, the plastic buffer body has a circumferential guide ring and a spherical guide stop at one end, wherein an opening for the ram is formed lying opposite the guide stop. The edge of the opening bears on a shell, which in turn bears on the inner side of the hollow ball segment, in such a way that the plastic buffer body with its guide stop is fixed under pretension in the head shaped as a ball segment.

The ram has a section, e.g. a threaded section, for fastening the mentioned rod-shaped connector.

Grooves or recesses are formed in the guide ring and/or guide stop for fluid passage.

Via the design of the plastic buffer body regarding geometry and/or material, radial, tensile and compressive forces and lifting and pivoting movements of the ram and the connector fixed thereto may be predefined that can be achieved in this respect.

In one embodiment of the invention, the plastic buffer body is made of polycarbonate urethane (PCU) or similar plastics.

The hollow ball segment is secured within the head shaped as a ball segment by means of a clamping ring.

In one configuration of the invention, the hollow ball segment is made of titanium material or a titanium alloy. The shell itself may likewise be made of a titanium alloy, but may also be manufactured from a ceramic material.

The threaded screw shank of the pedicle screw preferably has a self-tapping thread with a small pitch for an optimum screw-in position.

In one configuration of the invention, the plastic buffer body has an access to the head of the ram in the area of the guide stop. In the head of the ram, a recess with a contour for receiving a tool may be introduced in order to enable counterpressure to be exerted when the connector is mounted to the ram.

In one further development according to the invention, the head shaped as a ball segment is formed to be divided. The dividing is preferably made such that as a result, there will be two semi-spheres or semi-sphere segments equipped with means along their separation line which permit a form-fit connection of the half-shells to be caused. These may be locking means and counterlocking means. The connection is preferably made by using the principle of a bayonet lock.

The invention will be explained below in more detail by means of an exemplary embodiment and with the aid of Figures.

Shown are in.

The polyaxial pedicle screw according to the invention as shown in the Figures comprises a head 1 shaped as a ball segment, which head merges into a threaded screw shank 10 in its base portion.

Into the head 1 shaped as a ball segment, a hollow ball segment 3 is inserted which comprises a recess for receiving a rod-shaped connector 7. The hollow ball segment 3 is pivotable within the head 1 shaped as a ball segment. Corresponding pivoting and rotating movements of the connector 7 may be performed in this respect.

In the direction of the longitudinal axis of the threaded screw shank 10, the head 1 shaped as a ball segment has a cutout 8 with an inner thread.

Figure 4:
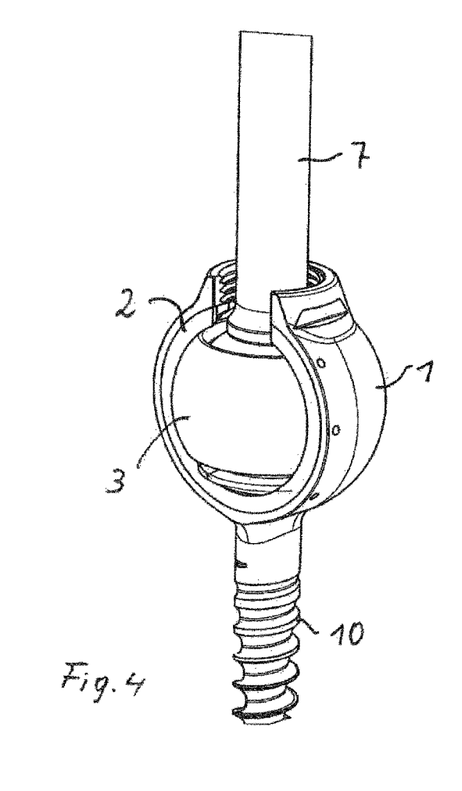
FIG. 4 a representation of the arrangement of the connector pivoted into the cutout for the purpose of screwing in the implant in an unimpeded manner.

During the screwing in of the pedicle screw, the connector together with the hollow ball segment is brought into such a position that the connector comes to rest within the cutout 8.

Figure 1A:
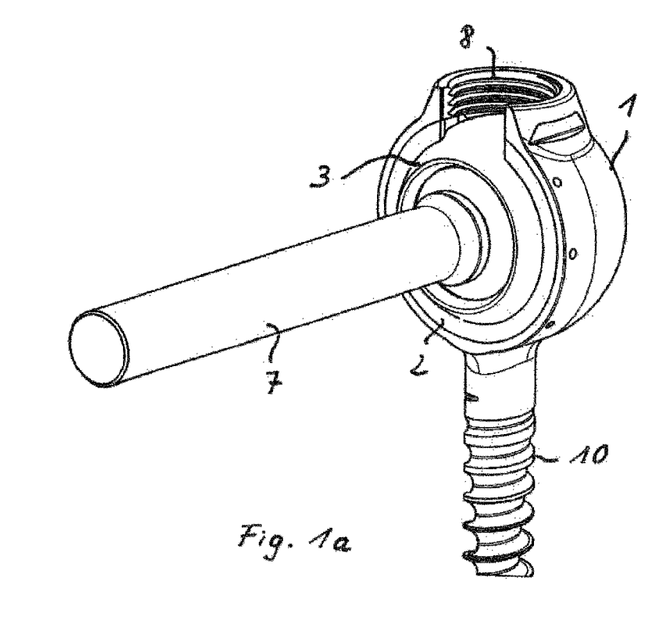
FIGS. 1a and 1b a perspective view and a sectional view of the polyaxial pedicle screw according to the invention with the connector, ram and plastic buffer body being indicated.
Figure 1B:
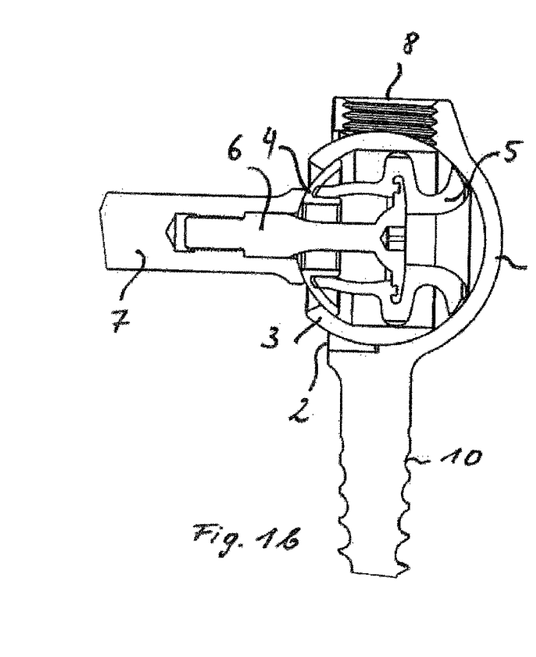
Figure 2A:
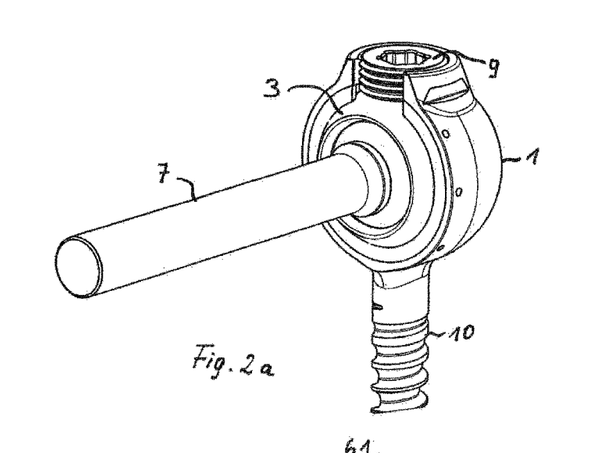
FIGS. 2a and 2b a perspective view and a sectional view similar to that of FIGS. 1a and 1b, but with a grub screw being introduced in the cutout with the inner thread in the head shaped as a ball segment.
Figure 2B:
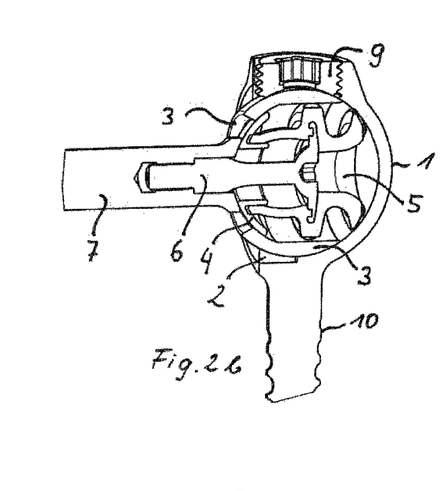

After screwing the pedicle screw into the bone material, in particular vertebral body material, the connector may be positioned in the location as then required, wherein a grub screw 9 permits the hollow ball segment 3 to be blocked via an inner thread in the cutout 8, wherein the connector 7 as well is positionally fixed. The rod remains pivotable relative to the hollow ball even after fixing of the hollow ball segment 3.

In the hollow ball segment 3, a plastic buffer body 5 is situated which is in communication with a ram 6, wherein the ram 6 has a head 61 which engages in an associated annular groove in the plastic buffer body or is overmolded by the plastic buffer body in the head portion 61.

Figure 5:
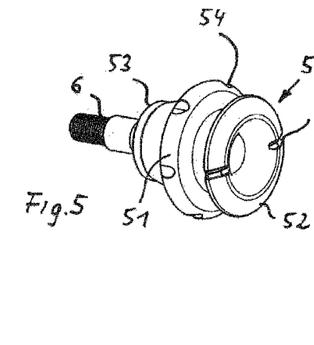
FIG. 5 a perspective representation of the plastic buffer body with a ram.

The plastic buffer body 5 has a circumferential guide ring 51 and a spherical guide stop 52 at one end. An opening for the ram 6 is formed in the plastic buffer body 5 lying substantially opposite the guide stop 52.

Figure 6:
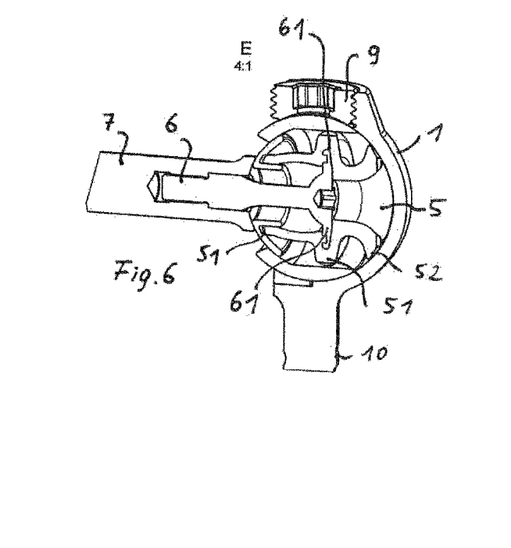
FIG. 6 a detailed representation of the pedicle screw in a sectional view.

The edge 53 of the opening of the plastic buffer body 5 is supported on a shell 4, which in turn bears on the inner side of the hollow ball segment 3, and namely in such a way that the plastic buffer body 5 with its guide stop 52 is fixed under pretension in the head shaped as a ball segment. Due to the elastic properties of the plastic buffer body 5, the movability of the ram and thus of the connector 7 is maintained so that physiological movements may be performed by an optional change of length and simultaneous tilting of the connector in relation to the fixed screw. Due to that, the arrangement can follow the existing movements in the spinal column such as flexion, extension, lateral tilt and rotation.

Due to the construction according to the invention, the plastic buffer body 5 is only subjected to compressive load so that possible wear is reduced.

Grooves or cutouts 54 are formed in the guide ring 51 and/or guide slot 52 for fluid passage. Entered fluids may thus overflow with respect to the cutout 54. Moreover, the action of the plastic buffer body 5 may be influenced in a targeted manner.

Via the design configuration of the plastic buffer body 5, there is the option of individually setting the tensile and compressive side and thus to vary both maximum strokes and forces and the force progression. This allows changes of length and movement abilities of the connector to be defined in a targeted manner. By varying the configuration of the plastic buffer body 5, also with regard to the material selection, an initially linear and subsequently progressive force progression may be realized.

A targeted pretension when inserting the plastic buffer body in the hollow space of the ball anticipates a setting or creeping of the material so that the necessary long-term stability and a reproducible behavior are guaranteed.

The hollow ball segment 3 is secured in the head 1 shaped as a ball segment by means of a clamping ring 2.

In a preferred configuration, the plastic buffer body 5 has an access to the head 61 of the ram 6 in the area of the guide stop 52 in order to introduce a tool in a recess present therein.

The ball-shaped head of the pedicle screw fixes all of the components that are necessary for the solution according to the invention. The clamping ring 2 holds these components inside the head of the pedicle screw. The clamping ring 2 may be fixed e.g. by dowel pins, but may also be fastened in a material-fit manner by means of laser welding, for example.

The hollow ball segment 3 virtually represents an inner sleeve and forms the front half of the entire ball closing the open part of the head in the shape of a ball segment and clamps the remaining components inside the head.

Figure 3A:
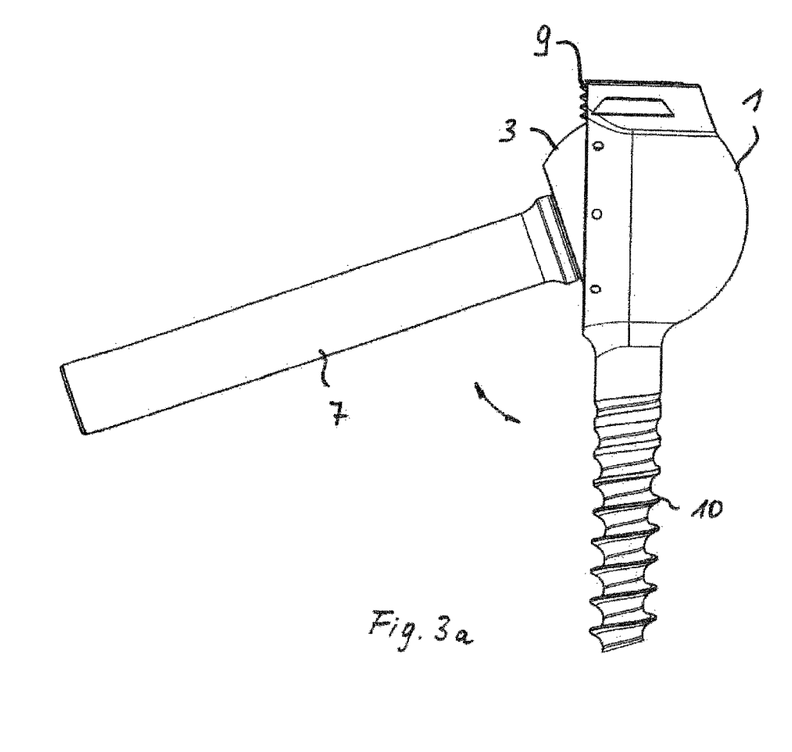
FIGS. 3a and 3b various perspective views with a polyaxial pivoting of 20° between the longitudinal axis of the threaded screw shank and the connector.
Figure 3B:
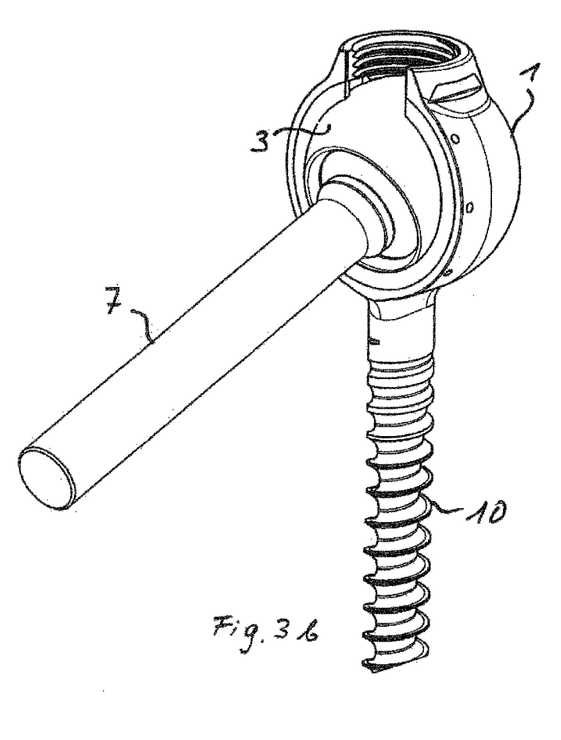

During the operation in using the pedicle screw, the inner sleeve allows the angle between the rod and the pedicle screw to be adjusted in the range from about ±20° in any arbitrary direction, whereby the desired polyaxial function is guaranteed. Incidentally, the fixing within the framework of this mobility is not subject to stress. Moreover, the inner sleeve forms a counter-bearing for the movement of the supporting shell 4 and the plastic buffer body 5. As already explained, the inner sleeve 3 is fixed by means of the grub screw 9 or a similar means at the end of the implantation. After fixing the hollow ball segment 3 by the mentioned grub screw 9, the plastic buffer body with the connected connector 7 and shell 4 remains pivotable within the hollow ball segment 3 and thus compensates for misalignments which are still existing.

The shell 4 closes the remaining opening and constitutes a counter-bearing for the plastic buffer body 5 which is brought to compression. When the entire arrangement is moved postoperatively, it will serve as a sliding partner for the inner sleeve, i.e. for the hollow ball segment 3.

The actual element of motion is formed by the plastic buffer body 5, and namely in case of tension and compression on the ram or the connector 7.

According to one exemplary embodiment of the invention, the created geometry in conjunction with the employed material polycarbonate urethane allows the system to be shortened by about 2.2 mm and lengthened by about 2.8 mm.

Due to the configuration of the ram 6 with head 61, the plastic buffer body 5 is only subjected to compressive load.

The connector 7 functions as a connecting element to the next pedicle screw of an arbitrary system. For the purpose of implantation, the rod is pivotable upward into the cutout 8 with all of the components connected thereto so as to enable the already mentioned screwing in of the pedicle screw.

Figure 7:
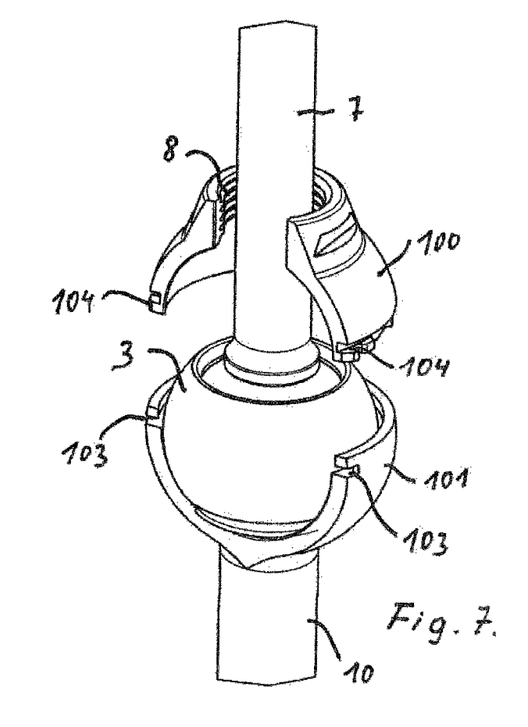
FIG. 7 a representation of the inventive pedicle screw with the head in the shape of a ball segment, which head is divided into two half-shells or half-shell segments, wherein the segments or half-shells are configured to be connectable by locking means and counterlocking means, in a separate position, and FIG. 8 a representation similar to that of FIG. 7 but with the position of the half-shells being coherent.
Figure 8:
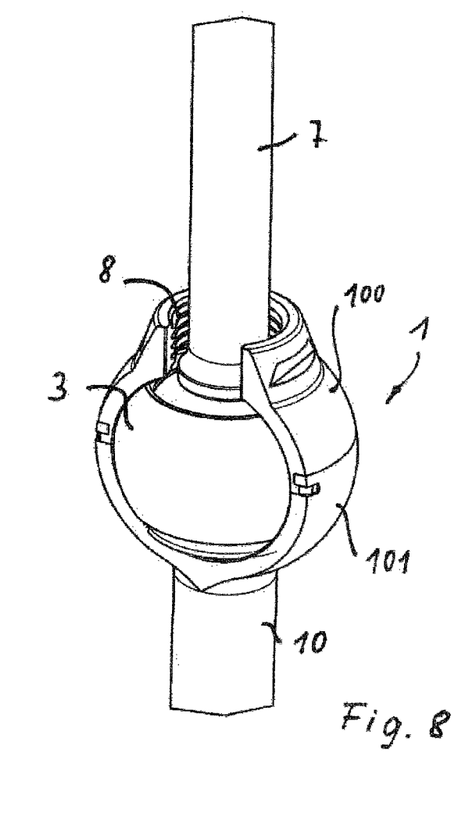

FIGS. 7 and 8 show a further development of the invention with a pedicle screw which has a head 1 realized in the shape of a ball segment and composed of two half-shells or half-shell segments 100; 101.

The two half-shells 100; 101 have complementary locking means 103 and counterlocking means 104 so as to join them in a form-fit and/or force-fit manner. This form-fit and/or force-fit joining preferably is made using the principle of a known bayonet lock.

The invention claimed is:

1. A polyaxial pedicle screw with a head (1) in the shape of a ball segment and with a threaded screw shank (10), wherein a hollow ball segment (3) with a recess for receiving a rod-shaped connector (7) is mounted in the head, in order to permit pivoting movements and rotation movements of the connector (7), wherein moreover, in the direction of the longitudinal axis of the threaded screw shank (10), the head (1) in the shape of a ball segment has a cutout (8) with an inner thread in which the rod-shaped connector (7) can be moved in and out and, by means of the inner thread in the cutout (8), a grub screw (9) can be introduced for blocking the hollow ball segment (3),
characterized in that
an elastic plastic buffer body (5) is fitted in the hollow ball segment (3) and is connected to a ram (6), wherein the ram (6) has a head (61) which engages in an associated annular groove in the plastic buffer body or which is at least in part surrounded by the plastic buffer body, the plastic buffer body (5) moreover has a circumferential guide ring (51) and a spherical guide stop (52) at one end, wherein an opening for the ram (6) is formed lying opposite the guide stop (52), and the edge (53) of the opening bears on a shell (4), which in turn bears on the inner side of the hollow ball segment (3), in such a way that the plastic buffer body (5) with its guide stop (52) is fixed under pretension in the head (1) shaped as a ball segment.

2. The polyaxial pedicle screw according to claim 1, characterized in that
the ram (6) has a section for fastening the rod-shaped connector (7).

3. The polyaxial pedicle screw according to claim 1, characterized in that
grooves or cutouts (54) are formed in the guide ring (51) and/or guide stop (52) for fluid passage.

4. The polyaxial pedicle screw according to claim 1, characterized in that
the plastic buffer body (5) is made of polycarbonate urethane (PCU).

5. The polyaxial pedicle screw according to claim 1, characterized in that
the hollow ball segment (3) is secured within the head (1) shaped as a ball segment by means of a clamping ring (2).

6. The polyaxial pedicle screw according to claim 1, characterized in that
the hollow ball segment (3) is made of a titanium material or a titanium alloy.

7. The polyaxial pedicle screw according to claim 1, characterized in that
the shell (4) is made of a titanium alloy or a ceramic material.

8. The polyaxial pedicle screw according to claim 1, characterized in that
the threaded screw shank (10) has a self-tapping thread.

9. The polyaxial pedicle screw according to claim 1, characterized in that
the guide stop (52) has an access to the head (61) of the ram (6).

10. The polyaxial pedicle screw according to claim 1, characterized in that the head (1) in the shape of a ball segment is formed to be divided.

11. The polyaxial pedicle screw according to claim 10, characterized in that
the head (1) in the shape of a ball segment is composed of two half-shells (100; 101).

12. The polyaxial pedicle screw according to claim 11, characterized in that
the half-shells (100; 101) are joined by locking means and counterlocking means (103; 104) in a form-fit manner.

13. The polyaxial pedicle screw according to claim 10, characterized in that
the head (1) in the shape of a ball segment is formed to be divided in two.

\* \* \* \* \*